(12) United States Patent
Teicher et al.

(10) Patent No.: US 6,685,652 B1
(45) Date of Patent: Feb. 3, 2004

(54) METHOD FOR DETERMINING FLUCTUATION IN ATTENTIONAL STATE AND OVERALL ATTENTIONAL STATE

(75) Inventors: Martin H. Teicher, Rye, NH (US); Steven B. Lowen, Burlington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 159 days.

(21) Appl. No.: 09/860,701

(22) Filed: May 17, 2001

Related U.S. Application Data

(60) Provisional application No. 60/204,663, filed on May 17, 2000.

(51) Int. Cl.⁷ .............................. A61B 13/00; A61B 5/00
(52) U.S. Cl. ....................................... 600/558; 600/559
(58) Field of Search ................................ 600/587–595, 600/558, 300, 559; 434/236

(56) References Cited

U.S. PATENT DOCUMENTS

| | | | |
|---|---|---|---|
| 4,770,636 A | | 9/1988 | Buschke ..................... 434/236 |
| 5,142,590 A | | 8/1992 | Carpenter et al. ............ 382/14 |
| 5,295,491 A | * | 3/1994 | Gevins ........................ 600/544 |
| 5,377,100 A | | 12/1994 | Pope et al. .................. 364/410 |
| 5,795,155 A | | 8/1998 | Morrel-Samuels ........... 434/107 |
| 5,801,810 A | | 9/1998 | Roenker ...................... 351/246 |
| 5,940,801 A | | 8/1999 | Brown .......................... 705/2 |
| 5,983,129 A | | 11/1999 | Cowan et al. ............... 600/544 |
| 6,053,739 A | * | 4/2000 | Stewart et al. .............. 434/236 |
| 6,113,538 A | | 9/2000 | Bowles et al. .............. 600/300 |
| 6,231,187 B1 | * | 5/2001 | Munoz et al. .............. 600/558 |
| 6,241,686 B1 | | 6/2001 | Balkin et al. ................ 600/544 |
| 6,334,778 B1 | * | 1/2002 | Brown ........................ 434/258 |

OTHER PUBLICATIONS

Greenberg, "An objective measure of methylphenidate response: clinical use of the MCA," *Psychopharmacology Bulletin* 23:279–282 (1987).

Rosvold et al., "A continuous performance test of brain damage," *Journal of Consulting and Clinical Psychology* 20:343–350 (1956).

* cited by examiner

*Primary Examiner*—Eric F. Winakur
*Assistant Examiner*—David J. McCrosky
(74) *Attorney, Agent, or Firm*—Clark & Elbing, LLP

(57) ABSTRACT

The invention provides methods for determining shifts in the attentional state of a subject. These methods are useful for diagnosing subjects with a psychological or behavioral disorder. The invention also features methods for determining the effect of a therapy on the overall attentional state and shifts in the attentional state of a subject.

40 Claims, 2 Drawing Sheets

Figure 1

| MEASURES | ADHD | NL | F(1,66) = | p < | EFFECT SIZE |
|---|---|---|---|---|---|
| Standard CPT Parameters | | | | | |
| Errors of Commision | 27.9 ± 2.4 | 11.6 ± 6.6 | 5.38 | 0.03 | 0.89 |
| Errors of Omission | 13.1 ± 1.8 | 1.2 ± 4.9 | 5.20 | 0.03 | 0.87 |
| Latency | 537 ± 101 | 619 ± 28 | 7.68 | 0.007 | 1.06 |
| Variability (S.D.) | 179 ± 7.2 | 134 ± 20 | 4.82 | 0.03 | 0.84 |
| Attention Shift Analysis | | | | | |
| Time on Task (%) | 42.6 ± 3.8 | 82.4 ± 10.4 | 12.95 | 0.0006 | 1.37 |
| Shifts (#) | 12.8 ± 0.6 | 5.4 ± 1.6 | 19.22 | 0.00004 | 1.67 |

METHOD FOR DETERMINING FLUCTUATION IN ATTENTIONAL STATE AND OVERALL ATTENTIONAL STATE

CROSS REFERENCE TO RELATED APPLICATIONS

This application claims priority to U.S. Ser. No. 60/204,663, filed May 17, 2000.

BACKGROUND OF THE INVENTION

A subject's visual attention can be tested by displaying a series of visual stimuli, to which the subject is instructed to respond. Typically, the stimuli are of two types, and the subject is instructed to respond to only one of them. Data are collected for each stimulus presented including the type of stimulus, whether or not the subject responded, and if so, how long the subject took to respond. The continuous performance attention task has been in use since the mid 50's (Rosvold et al., 1956, J. of Consulting and Clinical Psychology, 20: 343–350), with computerized versions available in the 1970's (Greenberg, 1987, 23: 279–282). The previous methods of analysis of the raw data generated from these methods have typically distilled the data into a few numbers which do not capture the subject's fluctuations in attention.

Another method for assessing the visual attention capabilities of a subject involves determining how long a particular visual stimulus must be present before a subject can detect it (U.S. Pat. No. 5,801,810). This method does not reveal the attentional state of the subject, rather, it requires the subject to be fully attentive.

Other reported methods determine a subject's intensity of focused attention, concentration, and/or interest by measuring signals naturally emanating from the brain (U.S. Pat. Nos. 5,983,129 and 5,377,100). These brainwaves vary across subjects and even within the same subject; thus, these methods do not provide a reliable, well-defined number for classifying attentional states.

A diagnostic assessment of psychological conditions can be made by conducting a sequence of continuous performance tasks where information is recorded to reflect the number of target stimuli correctly identified, the number of target stimuli missed, the number of responses to non-target stimuli, the number of non-target stimuli correctly missed, and the final interstimulus interval (U.S. Pat. No. 5,940,801). This method can be used in a clinical setting, as well as remote locations such as the home, school, or workplace. Using this method in remote locations is useful for psychological and behavioral problems that are highly stimulus-dependent and may not be manifested in a clinical environment, such as depression, anxiety, schizophrenia, addiction, eating disorders, attention deficit disorders, attention deficit and hyperactivity disorder. This method does not provide a way to classify performance into states.

The aforementioned methods do not accurately quantify a subject's attentional state. None classify a subject's behavior into specific well-defined states or examine fluctuations in attention over time.

SUMMARY OF THE INVENTION

In one aspect, the invention features a method of acquiring information about the attentional state of a subject. The method involves (a) presenting to the subject a sequence of a predetermined number of stimuli over a predetermined period of time, wherein the sequence includes target and nontarget stimuli, (b) scoring the response of the subject on the percentage of targets responded to and the percentage of nontargets responded to, and (c) on the basis of the scoring of step (b), making a determination of the attentional state of the subject.

This method can be used to assess both overall attention and impulsivity. This method can be repeated three or more times to determine the pattern of attentional states and the time spent in each state.

This method can be used to diagnose the subject being tested for a psychological, neurological, or behavioral disorder, such as depression, an anxiety disorder, schizophrenia, a drug addiction, an eating disorder, an attention deficit disorder, an attention deficit and hyperactivity disorder, a learning disorder, or Alzheimer's disease, dementia, epilepsy, stroke or traumatic brain injury. This method can be used to identify a subject at risk for a psychological, neurological, or behavioral disorder or to diagnose a subject with such a disorder. Additionally, this method can be used to determine the preferred therapy for the treatment of a psychological, neurological, or behavioral disorder or to correlate the attention state of a subject involved in a clinical trial of a therapy for a psychological or behavioral disorder with the success or failure of the therapy to improve the subject's condition.

This method can also be used to assess the eligibility of a subject to obtain a driver's license or a volunteer or paid position, including those that require a longer than average attention span, such as, an air traffic controller, pilot, emergency room doctor, surgeon, police officer, military officer, or fire-fighter.

In a related aspect, the invention features a method of determining whether a therapy affects the attentional state of a subject. This method involves (a) presenting to the subject undergoing treatment with the therapy a sequence of a predetermined number of stimuli over a predetermined period of time, wherein the sequence comprises target and nontarget stimuli, (b) scoring the response of the subject on the percentage of targets responded to and the percentage of nontargets responded to, and (c) on the basis of the scoring of step (b), making a determination of the attentional state of the subject. An altered attentional state, compared to either the attentional state of the subject when not undergoing treatment with the therapy or the attentional state of a control subject when not undergoing treatment with the therapy, indicates that the therapy affects the attentional state of the subject.

In one embodiment of this aspect, both overall attention and impulsivity are assessed. This method may be repeated three or more times to determine the pattern of attentional states and the time spent in each state. This method may also further include comparing the effect of the therapy on the attentional state of the subject to the effect of another therapy on the attentional state of the subject. Additionally, this method may further involve comparing the attentional state of a subject diagnosed with a disorder to that of a subject not diagnosed with the disorder.

In various embodiments, the subject is diagnosed with a psychological or behavioral disorder, such depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury. In other embodiments, the subject is involved in a clinical trial of a therapy for a psychological, neurological, or behavioral disorder. This method may be also used to determine the preferred therapy for the treatment of a psychological, neurological, or behavioral disorder.

In one desirable embodiment of any of the methods of the invention, the stimuli are visual symbols or audio sounds. The symbols can be individual numbers, letters, or shapes, or a combination of the above. Preferably, the stimuli are presented using a computer screen or speaker and the subject's responses are recorded using a computer. In another desirable embodiment of the invention, the stimuli number 15, 20, 30, or greater within each analysis period. The test may be conducted in a clinical setting or across a network.

BRIEF DESCRIPTION OF THE DRAWINGS

FIG. 1 is a table showing the assessment of the attentional state of children diagnosed with attention deficit hyperactivity disorder ("ADHD") and the attentional state of normal children not diagnosed with ADHD ("NL") using traditional continuous performance task (CPT) parameters and using the method of the present invention.

DETAILED DESCRIPTION

Figure 2:
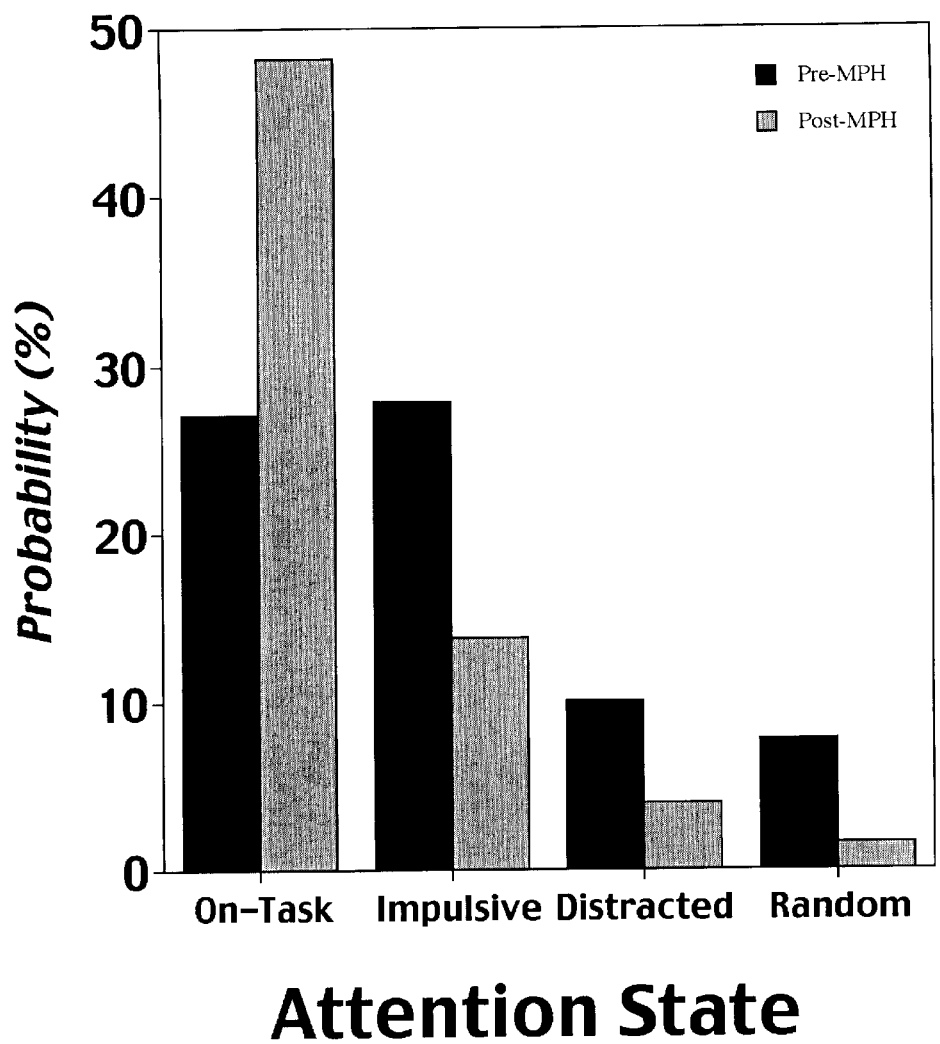
FIG. 2 is a bar graph of the probability of entering into one attentional state (i.e., "On Task," "Impulsive," "Distracted," or "Random" state) from any other attentional state based on 989 state entries in the premedicated state and 513 state entries after treatment with methylphenidate.

The invention features a method of assessing the attentional sate of a subject and measuring the fluctuations in the attentional state of the subject. This method determines both the impulsivity and overall attention of the subject and classifies the subject's attentional state accordingly. The invention also includes the novel method of determining and classifying the types and time course of fluctuations in attention state. Additionally, the invention includes a novel method of determining the effect of a therapy on the attentional state of a subject. The invention gives greater insight into the nature of the attentional process than prior methods which summarize the entire session or larger segments of the session into a set of measures.

This simple and rapid method of classifying behavior involves presenting a subject with a sequence of a predetermined number of stimuli over a predetermined period of time. These stimuli can be visual symbols or audio sounds, and they can be presented to the subject using a computer. The response of the subject is scored based on the percentage of target stimuli responded to and the percentage of nontarget stimuli responded to.

The following examples are to illustrate the invention; they are not meant to limit the invention in any way.

Assessment of Attentional State During a Computerized Task

A sequence of 15 stimuli are presented sequentially at two second intervals, over a total duration of 30 seconds. Each of the stimuli is either a target or a nontarget stimulus, chosen randomly with equal probability, and chosen independently of the other stimuli. Although the total number of symbols remains fixed at 15, the numbers of target and non-target symbols vary, but generally do not differ by more than about 5. The percentage of targets to which the subject responds is calculated, and denoted T. Similarly, the percentage of responses to non-targets is denoted N.

If a subject does not discriminate between targets and non-targets, then the two percentages T and N will be similar. A subject is defined to be "Randomly" responding if N and T differ by less than 25%, and the subject responds to most of the stimuli. Conversely, a subject is "Minimally responding" if N and T agree within 25% but the subject responds to less than half of the stimuli.

For a perfect response, T is 100%, and N is 0%. A subject is defined to be "On Task" if T is 85% or greater, and N is 20% or less. An impulsive subject typically responds to target stimuli with good accuracy, but exhibits errors of commission. If T is 85% or greater and N exceeds 20% (and the subject is not Randomly responding), then the subject is defined to be "Impulsive." A subject who misses more than 15% of the target stimuli (T is less than 85%), responds to a greater percentage of target than non-target stimuli (T is greater than N) and is not Randomly or Minimally responding, is defined as "Distracted."

Finally, a subject could respond to more non-target than target stimuli, either intentionally or through confusion. If N exceeds T by more than 25%, then the subject is defined to be "Contrary."

The above procedure is repeated using additional blocks of symbols of the same length. Thus, the attention state can be recorded after each block and used to determine the amount of time spent in each state, the pattern of attention states, and the range of attention states occupied by the subject.

Comparison of the Fluctuations in Attentional State of Subjects Diagnosed With Attention Deficit Hyperactivity Disorder to That of Normal Subjects The attentional state of subjects diagnosed with attention deficit hyperactivity disorder (ADHD) and the attentional state of normal subjects were measured using a computer-driven vigilance task coupled to a high precision motion analysis system. The vigilance task required subjects to respond to the presentation of eight pointed stars and to withhold response to five pointed starts. These symbols were presented at random screen positions every other second for a period of 200 milliseconds (450 stimuli per test with a 50% probability of the target stimuli). The accuracy and response latency to each stimulus was recorded. For each successive 30 second segment, the response was divided into "On Task," "Impulsive," "Distracted," "Random Responding," "Minimal Responding," and "Contrary Responding" attentional states, based on the percent responses to targets and non-targets using the criteria described above.

To assess the effects of racemic methylphenidate (MPH, also called RITALIN) on attention, 60 boys (10.1±1.3 years of age) with ADHD (DSM-IV combined subtype based on standard diagnostic methods using K-SADS-E, which is the children's version of the schedule for affective disorders and schizophrenia) were studied off all medication. These children had previously taken MPH as their only treatment but had not taken MPH for at least 24 hours prior to this study. Thus, these children had an undetectable level of MPH in their bloodstream. The children were also retested 120 minutes after administration of a probe-dose of MPH (0.4 mg/kg PO). Comparisons were made to a new group of eight healthy normal male controls (11.3±2.0 years of age; p>0.2) without ADHD (based on an assessment using the K-SADS-E criteria) (FIG. 1).

On average, unmedicated children with ADHD had 12.8 shifts between different attention states compared to only 5.4 shifts in controls ($F[1,66]=19.2$, $p<0.0001$). Following treatment with MPH, the attentional state of the children with ADHD shifted only 7.0 times per test ($F[1,59]=67.7$, $p<10$-

10), which was not significantly different than the number of times the control children without ADHD changed attentional states (p>0.4). Prior to treatment with MPH, children with ADHD were "On Task" during only 42.6% of the 30 second epochs vs. an 82.4% "On Task" rate for control children (F[1,66]=12.9, p<0.001). After treatment with MPH, the "On Task" rate increased to 75.4% ($p<10^{-11}$). As shown in FIG. 1, the number of shifts in attention state ("Shifts" row) and the percent of attention states that satisfied the "On Task" criteria ("Time on Task" row) were more robust indicators of the differences between ADHD children and normal controls ("NL" column) than traditional continuous performance task (CPT) parameters.

MPH markedly increased the likelihood that children with ADHD would persist in an "On Task" state (Chi squared, $p<10^{-20}$) and attenuated their proclivity to persist in a "Distracted" state (Chi squared, p<0.003). MPH did not significantly affect the probability that they would persist in an "Impulsive" or "Random" response state (both p>0.2). However, MPH significantly attenuated their proclivity to enter into an "Impulsive" or "Random" states from another attentional state (both $p<10^{-15}$; FIG. 2). These results illustrate the ability of the methods of the present invention to determine the effect of a therapy on the attentional state of a subject.

Other Embodiments

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each individual publication was specifically and individually indicated to be incorporated by reference.

What is claimed is:

1. A method of acquiring information about the pattern or fluctuation in attentional state of a subject, said method comprising:
   (a) presenting to said subject a sequence comprising target and nontarget stimuli, wherein said sequence is divided into three or more epochs in which there are a predetermined number of target and nontarget stimuli over a predetermined period of time;
   (b) scoring the response of said subject on the percentage of targets responded to and the percentage of nontargets responded to during each epoch; and
   (c) on the basis of the scoring of step (b), making a determination of the attentional state of said subject during each epoch; whereby the pattern or fluxuation in attentional states during the test period is assessed.

2. The method of claim 1, wherein the determination of step (c) comprises assessing both overall attention and impulsivity.

3. The method of claim 2, wherein steps (a) and (b) are repeated three or more times, whereby the pattern of attentional states and the length of time spent in each state is assessed.

4. The method of claim 1, wherein said stimuli are visual symbols.

5. The method of claim 4, wherein said visual symbols comprise individual numbers, letters, or shapes, or a combination thereof.

6. The method of claim 1, wherein said stimuli are audio sounds.

7. The method of claim 1, wherein said method is used to diagnose a neurological, psychological, or behavioral disorder.

8. The method of claim 7, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke or traumatic brain injury.

9. The method of claim 1, further comprising:
   (d) comparing the determination of step (c) in subjects diagnosed with a disorder and subjects not diagnosed with said disorder.

10. The method of claim 1, wherein said subject is involved in a clinical trial of a therapy for a psychological, neurological, or behavioral disorder.

11. The method of claim 1, wherein said method is used to determine the preferred therapy for the treatment of a psychological, neurological, or behavioral disorder.

12. The method claim 1, wherein said stimuli are presented using a computer screen or speaker and each subject's responses are stored in a computer.

13. The method of claim 1, wherein said subject communicates with a test administrator across a network.

14. The method of claim 1, wherein the results of said method are used in determining the eligibility of said subject to obtain a driver's license.

15. The method of claim 1, wherein the method is used to evaluate the subjects suitability for a position as an air traffic controller, pilot, emergency room doctor surgeons, police officer, military officer, or fire-fighter.

16. The method of claim 1, wherein the method is used to evaluate readiness of a subject to start school or to be promoted to the next grade or level.

17. The method of claim 1, wherein the number of stimuli is 15 or greater.

18. The method of claim 1, wherein said epochs are the same length.

19. A method of determining whether a therapy affects the attentional state of a subject, said method comprising:
   (a) presenting to said subject undergoing treatment with said therapy a sequence comprising target and nontarget stimuli, wherein said sequence is divided into three or more epochs in which there are a predetermined number of target and nontarget stimuli over a predetermined period of time;
   (b) scoring the response of said subject on the percentage of targets responded to and the percentage of nontargets responded to during each epoch; and
   (c) on the basis of the scoring of step (b), making a determination of the attentional state of said subject during each epoch; whereby the pattern in attentional states during the test period is assessed, wherein an altered pattern of attentional states, compared to either the pattern of attentional states of said subject when not undergoing treatment with said therapy, or the pattern of attentional states of a control subject when not undergoing treatment with said therapy, indicates that said therapy affects the pattern of attentional states of said subject.

20. The method of claim 19, wherein the determination of step (b) comprises assessing both overall attention and impulsivity.

21. The method of claim 20, wherein steps (a) and (b) are repeated three or more times, whereby the pattern of attentional states and the length of time spent in each state is assessed.

22. The method of claim 19, further comprising:
   (d) comparing the effect of said therapy on the attentional state of said subject to the effect of another therapy on the attentional state of said subject.

23. The method of claim 19, wherein said stimuli are visual symbols.

24. The method of claim 19, wherein said visual symbols comprise individual numbers, letters, or shapes, or a combination thereof.

25. The method of claim 19, wherein said stimuli are audio sounds.

26. The method of claim 19, wherein said subject is diagnosed with a neurological, psychological, or behavioral disorder.

27. The method of claim 26, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke or traumatic brain injury.

28. The method of claim 19, further comprising:
    (d) comparing the determination of step (c) in subjects diagnosed with a disorder and subjects not diagnosed with said disorder.

29. The method of claim 19, wherein said subject is involved in a clinical trial of a therapy for a psychological, neurological, or behavioral disorder.

30. The method of claim 19, wherein said method is used to determine the preferred therapy for the treatment of a psychological, neurological, or behavioral disorder.

31. The method claim 19, wherein said stimuli are presented using a computer screen or speaker and each subject's responses are stored in a computer.

32. The method of claim 19, wherein said subject communicates with a test administrator across a network.

33. The method of claim 19, wherein the number of stimuli is 15 or greater.

34. The method of claim 19, wherein said epochs are the same length.

35. A method of acquiring information about the attentional state of a subject, said method comprising:
    (a) presenting to said subject a sequence comprising target and nontarget stimuli, wherein said sequence is divided into three or more epochs in which there are a predetermined number of target and nontarget stimuli over a predetermined period of time;
    (b) scoring the response of said subject on the percentage of targets responded to and the percentage of nontargets responded to during each epoch; and
    (c) on the basis of the scoring of step (b), making a determination of the attentional state of said subject during each epoch; whereby the length of time spent in a particular attentional state during the test period is assessed.

36. The method of claim 35, wherein said epochs are the same length.

37. A method of determining whether a therapy affects the attentional state of a subject, said method comprising:
    (a) presenting to said subject undergoing treatment with said therapy a sequence comprising target and nontarget stimuli, wherein said sequence is divided into three or more epochs in which there are a predetermined number of target and nontarget stimuli over a predetermined period of time;
    (b) scoring the response of said subject on the percentage of targets responded to and the percentage of nontargets responded to during each epoch; and
    (c) on the basis of the scoring of step (b), making a determination of the attentional state of said subject during each epoch; whereby the length of time spent in a particular attentional state during the test period is assessed, wherein an length of time spent in a particular attentional state, compared to either the length of time spent in a particular attentional state of said subject when not undergoing treatment with said therapy or the length of time spent in a particular attentional state of a control subject when not undergoing treatment with said therapy, indicates that said therapy affects the length of time spent in a particular attentional state of said subject.

38. The method of claim 37, wherein said epochs are the same length.

39. A method of acquiring information about the attentional state of a subject, said method comprising:
    (a) presenting to said subject a sequence of a predetermined number of stimuli over a predetermined period of time, wherein said sequence comprises target and nontarget stimuli;
    (b) scoring the response of said subject on the percentage of targets responded to (T) and the percentage of nontargets responded to (N); and
    (c) on the basis of the scoring of step (b), making a determination of the attentional state of said subject, wherein said attentional state is selected from the group consisting of: a first attentional state characterized by N and T differing by less than 25% and said subject responding to more than half of the stimuli; a second attentional state characterized by N and T differing by less than 25% and said subject responding to less than half of the stimuli; a third attentional state characterized by T being 85% or greater and N being 20% or less; a fourth attentional state characterized by T being 85% or greater and N exceeding 20%; a fifth attentional state characterized by T being less than 85%, T being greater than N, and said subject not being in said first or second attentional state; and a sixth attentional state characterized by N exceeding T by more than 25%.

40. A method of determining whether a therapy affects the attentional state of a subject, said method comprising:
    (a) presenting to said subject undergoing treatment with said therapy a sequence of a predetermined number of stimuli over a predetermined period of time, wherein said sequence comprises target and nontarget stimuli;
    (b) scoring the response of said subject on the percentage of targets responded to (T) and the percentage of nontargets responded to (N); and
    (c) on the basis of the scoring of step (b), making a determination of the attentional state of said subject, wherein said attentional state is selected from the group consisting of: a first attentional state characterized by N and T differing by less than 25% and said subject responding to more than half of the stimuli; a second attentional state characterized by N and T differing by less than 25% and said subject responding to less than half of the stimuli; a third attentional state characterized by T being 85% or greater and N being 20% or less; a fourth attentional state characterized by T being 85% or greater and N exceeding 20%; a fifth attentional state characterized by T being less than 85%, T being greater than N, and said subject not being in said first or second attentional state; and a sixth attentional state characterized by N exceeding T by more than 25%; and wherein an altered attentional state, compared to either the attentional state of said subject when not undergoing treatment with said therapy or the attentional state of a control subject when not undergoing treatment with said therapy, indicates that said therapy affects the attentional state of said subject.

* * * * *